(12) United States Patent
Burton et al.

(10) Patent No.: US 7,364,540 B1
(45) Date of Patent: *Apr. 29, 2008

(54) IMPLANTABLE DEVICE AND METHOD FOR ADJUSTABLY RESTRICTING A BODY LUMEN

(75) Inventors: John H. Burton, Minnetonka, MN (US); Timothy C. Cook, Wayzata, MN (US)

(73) Assignee: Uromedica, Inc., Plymouth, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/477,977

(22) Filed: Jan. 5, 2000

Related U.S. Application Data

(63) Continuation of application No. 08/873,444, filed on Jun. 12, 1997, now Pat. No. 6,045,498.

(51) Int. Cl.
*A61F 2/02* (2006.01)

(52) U.S. Cl. .................. 600/30; 623/14.13; 128/898; 128/DIG. 25

(58) Field of Classification Search ............ 600/29–31; 606/191–193, 108; 128/DIG. 25; 604/96.01, 604/97.01, 97.02, 99.01, 102.01, 104, 164.02–164.04, 604/201, 215

See application file for complete search history.

(56) References Cited

U.S. PATENT DOCUMENTS 3,138,161 A   6/1964   Allen 4,019,499 A   4/1977   Fitzgerald (Continued)

FOREIGN PATENT DOCUMENTS

CA        2022709        2/1991

(Continued)

OTHER PUBLICATIONS

Lima, S., et al., "Further Experience with the Periurethral Expander: A new Type of Artificial Sphincter", *British Journal of Urology* (*1997*), 460-462.

(Continued)

*Primary Examiner*—Lee S. Cohen
(74) *Attorney, Agent, or Firm*—Schwegman, Lundberg, Woessner, & Kluth P.A.

(57) ABSTRACT

An implantable device and method for adjustably restricting a selected body lumen such as the urethra of a patient to treat urinary incontinence. The device includes an expandable element or membrane such as a balloon attached pressure-tightly to a flexible conduit at its forward end and includes a rear port portion containing an elastic septum and flow connected to the expandable element by a first passageway. The conduit contains a second passageway which allows it to be slid along an elongated guide probe initially inserted surgically into a patient's body adjacent the body lumen which is to be adjustably restricted. A suitable flowable material is injected from a syringe source into the device rear port sufficient to expand the membrane element and restrict the body lumen to the desired degree. The syringe and guide probe are removed and the skin incision is closed over the rear port end of the implanted device. The rear port septum is located under but near the patient's skin so that if it becomes necessary to post-operatively increase or decrease the degree of body lumen restriction it may be easily accessed with the needle of the syringe.

40 Claims, 4 Drawing Sheets

U.S. PATENT DOCUMENTS

| | | | |
|---|---|---|---|
| 4,553,959 A | 11/1985 | Hickey et al. ............... 604/96 |
| 4,559,043 A | 12/1985 | Whitehouse et al. ....... 604/201 |
| 4,669,478 A | 6/1987 | Robertson |
| 4,686,962 A | 8/1987 | Haber |
| 4,773,393 A | 9/1988 | Haber et al. ................. 600/30 |
| 4,784,660 A | 11/1988 | Fischell |
| 4,802,479 A | 2/1989 | Haber et al. ............... 128/344 |
| 4,817,637 A | 4/1989 | Hillegass et al. .......... 128/899 |
| 4,832,680 A | 5/1989 | Haber et al. ................. 600/31 |
| 4,846,784 A * | 7/1989 | Haber ................ 128/DIG. 25 |
| 4,857,041 A | 8/1989 | Annis et al. |
| 4,909,785 A | 3/1990 | Burton et al. ................. 604/54 |
| 4,938,760 A | 7/1990 | Burton et al. |
| 4,969,474 A | 11/1990 | Schwarz .................... 128/885 |
| 4,969,892 A | 11/1990 | Burton et al. |
| 5,012,822 A | 5/1991 | Schwarz .................... 128/885 |
| 5,041,136 A | 8/1991 | Wascher et al. |
| 5,047,055 A | 9/1991 | Bao et al. .................... 623/17 |
| 5,064,434 A | 11/1991 | Haber ........................ 623/11 |
| 5,066,303 A | 11/1991 | Bark et al. |
| 5,097,848 A | 3/1992 | Schwarz .................... 128/885 |
| 5,112,303 A | 5/1992 | Pudenz et al. ............... 604/49 |
| 5,123,428 A | 6/1992 | Schwarz .................... 128/885 |
| 5,133,753 A | 7/1992 | Bark et al. .................... 623/7 |
| 5,149,052 A | 9/1992 | Stoy et al. .................. 249/105 |
| 5,154,187 A | 10/1992 | Brownlee |
| 5,181,921 A | 1/1993 | Makita et al. .............. 606/195 |
| 5,192,326 A | 3/1993 | Bao et al. .................... 623/17 |
| 5,304,123 A | 4/1994 | Atala et al. ................... 604/54 |
| 5,334,153 A | 8/1994 | McIntyre et al. ............ 604/99 |
| 5,336,263 A | 8/1994 | Ersek et al. |
| 5,376,117 A | 12/1994 | Pinchuk et al. ................ 623/8 |
| 5,383,896 A | 1/1995 | Gershony et al. .......... 606/213 |
| 5,411,475 A | 5/1995 | Atala et al. ................... 604/54 |
| 5,437,603 A | 8/1995 | Cerny et al. ................. 600/29 |
| 5,451,406 A | 9/1995 | Lawin et al. |
| 5,480,430 A | 1/1996 | Carlisle et al. ................ 623/7 |
| 5,483,976 A | 1/1996 | McLaughlin et al. ....... 128/885 |
| 5,496,370 A | 3/1996 | Hamas ........................ 623/11 |
| 5,499,994 A | 3/1996 | Tihon et al. ................ 606/192 |
| 5,518,504 A | 5/1996 | Polyak |
| 5,520,700 A | 5/1996 | Beyar et al. |
| 5,534,023 A | 7/1996 | Henley .......................... 623/8 |
| 5,547,472 A | 8/1996 | Onishi et al. |
| 5,575,771 A | 11/1996 | Walinsky ..................... 604/96 |
| 5,578,009 A | 11/1996 | Kraus et al. .................. 604/96 |
| 5,634,877 A | 6/1997 | Salama ........................ 600/29 |
| 5,637,074 A | 6/1997 | Andino et al. ............... 600/29 |
| 5,647,836 A | 7/1997 | Blake, III et al. |
| 5,687,714 A | 11/1997 | Kolobow et al. |
| 5,749,826 A | 5/1998 | Faulkner |
| 5,830,228 A | 11/1998 | Knapp et al. ............... 606/195 |
| 5,938,669 A | 8/1999 | Klaiber et al. |
| 5,964,806 A | 10/1999 | Cook et al. ................... 623/14 |
| 5,976,186 A | 11/1999 | Bao et al. .................... 623/17 |
| 6,005,020 A | 12/1999 | Loomis ....................... 523/105 |
| 6,021,781 A | 2/2000 | Thompson et al. |
| 6,033,413 A | 3/2000 | Mikus et al. ................ 606/108 |
| 6,039,686 A | 3/2000 | Kovac |
| 6,042,536 A | 3/2000 | Tihon et al. |
| 6,045,498 A * | 4/2000 | Burton et al. ................. 600/30 |
| 6,050,937 A | 4/2000 | Benderev |
| 6,053,935 A | 4/2000 | Brenneman et al. |
| 6,095,969 A | 8/2000 | Karram et al. |
| 6,099,547 A | 8/2000 | Gellman et al. |
| 6,110,101 A | 8/2000 | Tihon et al. |
| 6,110,191 A | 8/2000 | Dehdashtian et al. |
| 6,117,067 A | 9/2000 | Gil-Vernet |
| 6,120,539 A | 9/2000 | Eldridge et al. ......... 623/11.11 |
| 6,132,465 A | 10/2000 | Ray et al. ................ 623/17.16 |
| 6,167,886 B1 | 1/2001 | Engel et al. |
| 6,171,231 B1 | 1/2001 | Connolly |
| 6,419,624 B1 | 7/2002 | Burton et al. |
| 6,419,701 B1 | 7/2002 | Cook et al. |
| 6,423,080 B1 | 7/2002 | Gellman et al. |
| 6,579,224 B1 | 6/2003 | Burton et al. |
| 6,645,138 B2 | 11/2003 | Cook et al. |
| 6,752,814 B2 | 6/2004 | Gellman et al. |
| 6,786,861 B1 | 9/2004 | Pretorius |
| 7,014,606 B2 | 3/2006 | Burton et al. |
| 2002/0055748 A1 | 5/2002 | Gellman et al. |
| 2002/0156342 A1 | 10/2002 | Burton et al. |
| 2004/0015045 A1 | 1/2004 | Burton et al. |
| 2004/0030207 A1 | 2/2004 | Gellman et al. |
| 2004/0230206 A1 | 11/2004 | Gellman et al. |
| 2005/0027161 A1 | 2/2005 | Cook et al. |
| 2005/0256364 A1 | 11/2005 | Burton et al. |
| 2006/0281964 A1 | 12/2006 | Burton et al. |

FOREIGN PATENT DOCUMENTS

| | | |
|---|---|---|
| EP | 0639355 | 8/1993 |
| EP | 078498 A2 | 7/1997 |
| EP | 0784987 | 7/1997 |
| EP | 0784987 2 | 7/1997 |
| EP | 0941712 | 8/1998 |
| WO | 91/00069 | 1/1991 |
| WO | WO91/00069 | 1/1991 |
| WO | WO-96/01597 | 1/1996 |
| WO | 98/20812 | 5/1998 |
| WO | 98/56311 | 12/1998 |
| WO | WO-00/18319 | 4/2000 |
| WO | WO-0066030 A1 | 11/2000 |

OTHER PUBLICATIONS lima, S.C., et al., "Combined Use of Enterocystoplasty and a new Type of Artificial Sphincter In The Treatment of Urinary Incontinence", *The Journal of Urology, vol. 156, Aug. 1996*, 622-624.

U.S. Appl. No. 10/673,028, filed May 5, 2003, Burton et al.

"U.S. Appl. No. 08/873,444 (Atty. Ref. 825.001US1) Final Office Action mailed Aug. 5, 1998", 9 pgs.

"U.S. Appl. No. 08/873,444 (Atty. Ref. 825.001US1) Final Office Action mailed Sep. 27, 1999", 6 pgs.

"U.S. Appl. No. 08/873,444 (Atty. Ref. 825.001US1) Non-Final Office Action mailed Jan. 13, 1998", 8 pgs.

"U.S. Appl. No. 08/873,444 (Atty. Ref. 825.001US1) Non-Final Office Action mailed Feb. 3, 1999", 6 pgs.

"U.S. Appl. No. 08/873,444 (Atty. Ref. 825.001US1) Non-Final Office Action mailed Feb. 4, 1999", 7 pgs.

"U.S. Appl. No. 08/873,444 (Atty. Ref. 825.001US1) Notice of Allowance mailed Feb. 22, 2000", 4 pgs.

"U.S. Appl. No. 08/873,444 (Atty. Ref. 825.001US1) Response to Final Office Action filed Nov. 1, 1999", 2 pgs.

"U.S. Appl. No. 08/873,444 (Atty. Ref. 825.001US1) Response to Final Office Action filed Nov. 5, 1998", 12 pgs.

"U.S. Appl. No. 08/873,444 (Atty. Ref. 825.001US1) Response to Final Office Action filed Dec. 3, 1998", 9 pgs.

"U.S. Appl. No. 08/873,444 (Atty. Ref. 825.001US1) Response to Non-Final Office Action filed May 13, 1998", 16 pgs.

"U.S. Appl. No. 08/873,444 (Atty. Ref. 825.001US1) Response to Non-Final Office Action filed Jul. 6, 1999", 6 pgs.

"U.S. Appl. No. 08/928,946 (Atty. Ref. 825.002US1) Notice of Allowance mailed May 3, 1999", 11 pgs.

"U.S. Appl. No. 09/345,884 (Atty. Ref. 825.002US1) Non-Final Office Action mailed Mar. 19, 2001", 8 pgs.

"U.S. Appl. No. 09/345,884 (Atty. Ref. 825.002US2) Non-Final Office Action mailed Sep. 29, 2000", 9 pgs.

"U.S. Appl. No. 09/345,884 (Atty. Ref. 825.002US2) Notice of Allowance mailed Feb. 11, 2002", 6 pgs.

"U.S. Appl. No. 09/345,884 (Atty. Ref. 825.002US2) Response to Non-Final Office Action filed Dec. 28, 2000", 7 pgs.

"U.S. Appl. No. 09/345,884 (Atty. Ref. 825.002US2) Response to Non-Final Office Action filed Jul. 13, 2001", 8 pgs.

"U.S. Appl. No. 10/167,565 (Atty. Ref. 825.002US3) Non-Final Office Action mailed Feb. 11, 2003", 6 pgs.

"U.S. Appl. No. 10/167,565 (Atty. Ref. 825.002US3) Notice of Allowance mailed May 30, 2003", 8 pgs.

"U.S. Appl. No. 10/167,565 (Atty. Ref. 825.002US3) Response to Non-Final Office Action filed May 9, 2003", 7 pgs.

"U.S. Appl. No. 10/673,028 (Atty. Ref. 825.002US4) Non-Final Office Action mailed Jun. 2, 2004", 7 pgs.

"U.S. Appl. No. 10/932,414 (Atty. Ref. 825.002US5) Final Office Action mailed Jun. 15, 2007", 9 pgs.

"U.S. Appl. No. 10/932,414 (Atty. Ref. 825.002US5) Non-Final Office Action mailed Feb. 12, 2007", 8 pgs.

"U.S. Appl. No. 10/932,414 (Atty. Ref. 825.002US5) Non-Final Office Action mailed Apr. 17, 2006", 9 pgs.

"U.S. Appl. No. 10/932,414 (Atty. Ref. 825.002US5) Notice of Allowance mailed Oct. 23, 2006", 5 pgs.

"U.S. Appl. No. 10/932,414 (Atty. Ref. 825.002US5) Response to Non-Final Office Action filed May 14, 2007", 8 pgs.

"U.S. Appl. No. 10/932,414 (Atty. Ref. 825.002US5) Response to Non-Final Office Action filed Jul. 7, 2006", 7 pgs.

"U.S. Appl. No. 10/932,414 (Atty. Ref. 825.002US5) Supplemental Notice of Allowability mailed Nov. 27, 2006", 2 pgs.

"U.S. App. No. 11/120,631 (Atty. Ref. 825.001US3) Non-Final Office Action mailed Aug. 24, 2006", 7 pgs.

"U.S. Appl. No. 09/416,193 (Atty. Ref. 825.006US1) Non-Final Office Action mailed Oct. 10, 2001", 6 pgs.

"U.S. Appl. No. 09/416,193 (Atty. Ref. 825.006US1) Non-Final Office Action mailed Mar. 27, 2001", 7 pgs.

"U.S. Appl. No. 09/416,193 (Atty. Ref. 825.006US1) Non-Final Office Action mailed Jul. 15, 2002", 6 pgs.

"U.S. Appl. No. 09/416,193 (Atty. Ref. 825.006US1) Response to Non-Final Office Action filed Nov. 15, 2002", 5 pgs.

"U.S. Appl. No. 09/416,193 (Atty. Ref. 825.006US1) Response to Non-Final Office Action filed Apr. 9, 2002", 15 pgs.

"U.S. Appl. No. 09/416,193 (Atty. Ref. 825.006US1) Response to Non-Final Office Action filed Jun. 26, 2001", 14 pgs.

"U.S. Appl. No. 10/167,563 (Atty. Ref. 825.007US2) Non-Final Office Action mailed Sep. 23, 2004", 9 pgs.

"U.S. Appl. No. 10/167,563 (Atty. Ref. 825.007US2) Response to Non-Final Office Action mailed Jan. 24, 2005", 12 pgs.

"U.S. Appl. No. 10/429,924 (Atty. Ref 825.006US2) Final Office Action mailed Dec. 13, 2006", 10 pgs.

"U.S. Appl. No. 10/429,924 (Atty. Ref. 825.006US2) Non-Final Office Action mailed Mar. 23, 2006", 12 pgs.

"U.S. Appl. No. 10/429,924 (Atty. Ref. 825.006US2) Response to Final Office Action filed Jun. 13, 2007", 8 pgs.

"U.S. Appl. No. 10/429,924 (Atty. Ref. 825.006US2) Response to Non-Final Office Action filed Sep. 22, 2006", 10 pgs.

"International Application No. PCT/US98/12368 (Atty. Ref. 825.002WO1) International Preliminary Examination Report mailed Sep. 20, 1999", 6 pgs.

"International Application No. PCT/US98/12368 (Atty. Ref. 825.002WO1) Written Opinion mailed Mar. 19, 1999", 6 pgs.

"Non-Final Office Action Mailed Sep. 14, 2007 in U.S. Appl. No. 10/932,414 (Atty. Ref. 825.002US5)", 11 pgs.

* cited by examiner

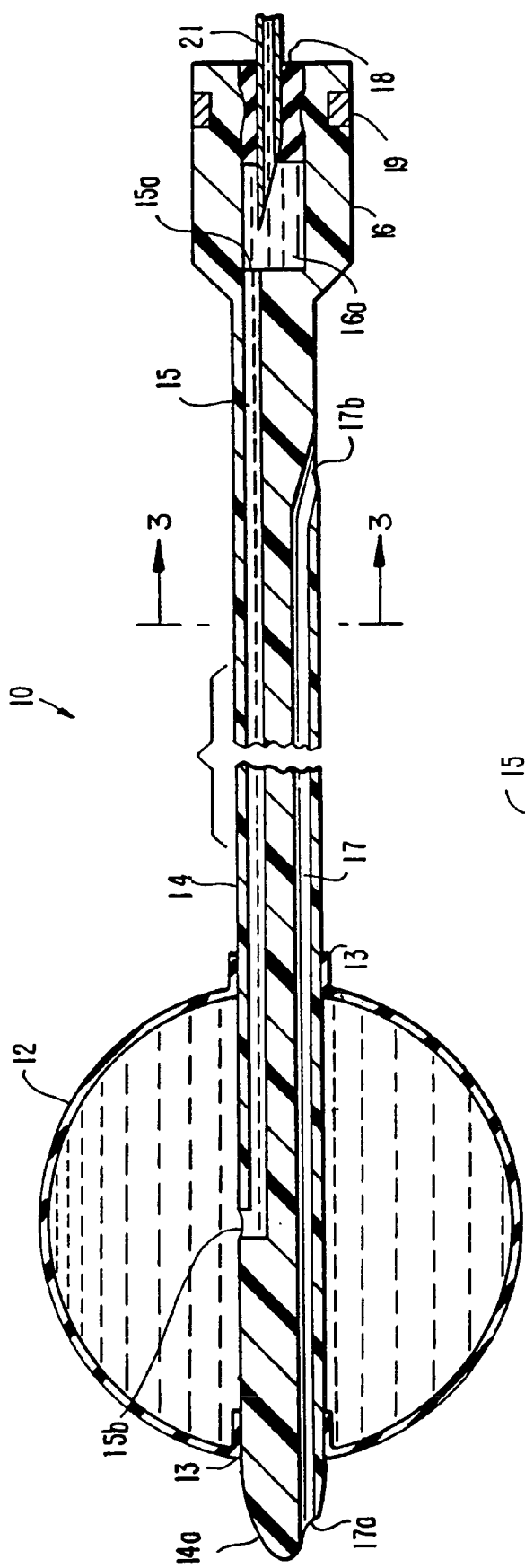

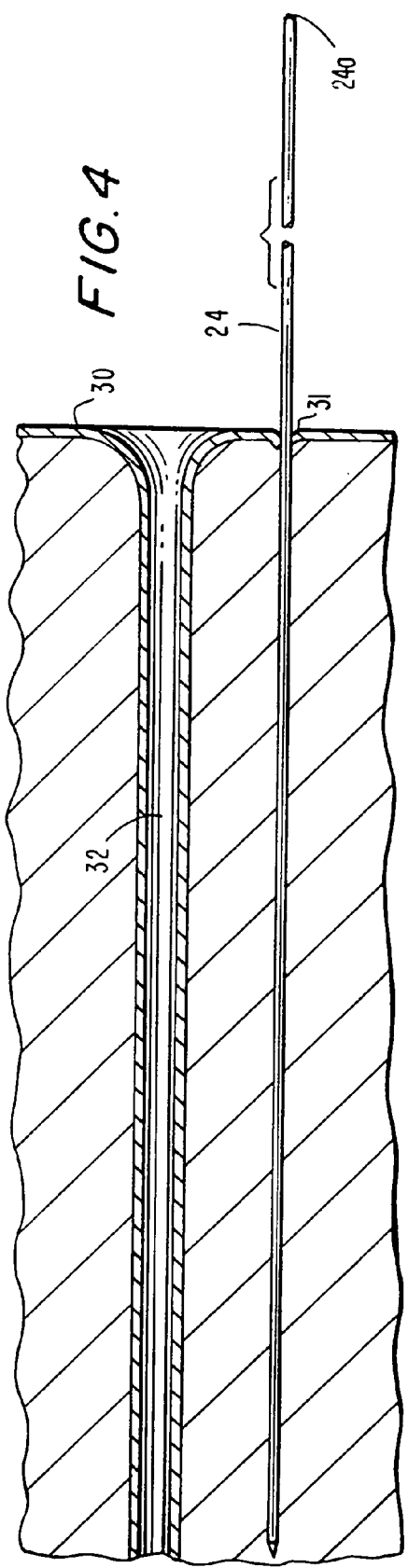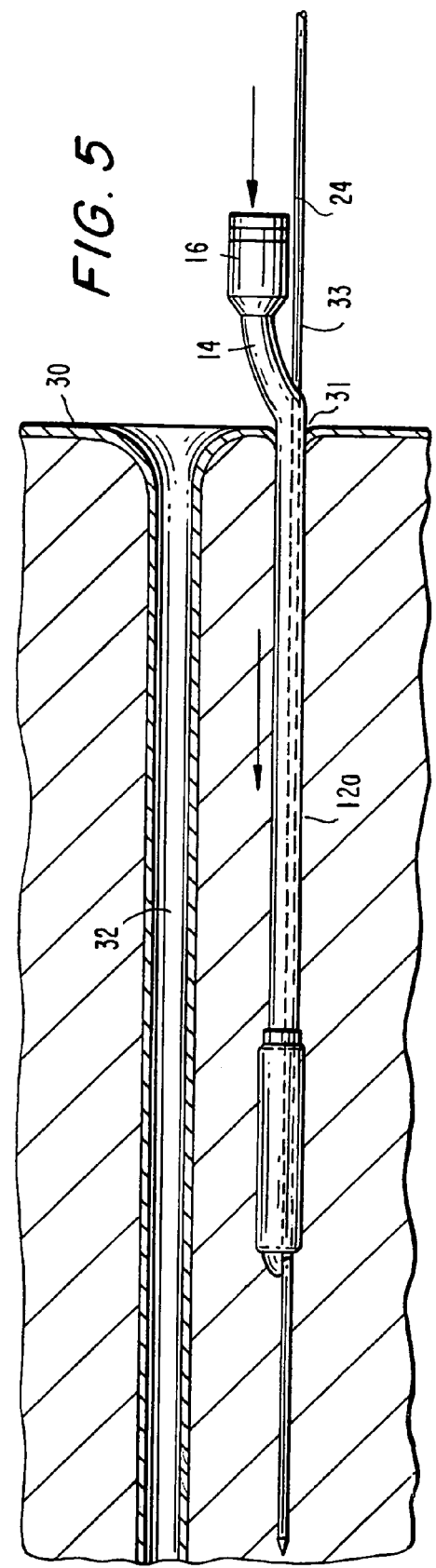

IMPLANTABLE DEVICE AND METHOD FOR ADJUSTABLY RESTRICTING A BODY LUMEN

This application is a Continuation of U.S. application Ser. No. 08/873,444 filed Jun. 12, 1997.

BACKGROUND OF INVENTION

The present invention pertains to an implantable device and method for adjustably restricting a body lumen such as the urethra by placing an expandable element having the form of a membrane or balloon adjacent to the body lumen. The invention also includes a device assembly and method for expansion of the expandable membrane element to cause displacement of the body tissue adjacent to the body lumen so as to adjustably restrict or coapt (close) the lumen. Expansion of the membrane element is accomplished by delivering a fluid material into a rear port of the implantable device remote from the expandable element but near the patient's skin, thus enabling post-operative adjustment with minimal surgical invasiveness.

Several devices for body lumen restriction to treat urinary incontinence are known and disclosed in the prior art, and have employed various means such as an outer tube for delivery of a detachable expandable membrane into body tissue. However, the known prior art devices do not provide any post-operative adjustability feature for introduction of new material into the expandable element to change the degree of restriction of a body lumen. These prior art devices have also proven to be of risk to the patient with respect to infection or migration back along the tract by which they were introduced through the body tissue. Such migration of the implantable device would render the treatment of incontinence ineffective and the device may even erode into the urinary tract causing infection and other severe complications.

For example, U.S. Pat. No. 4,733,393 to Haber et al discloses a hypodermically implantable genitourinary prosthesis which provides a extensible, inflatable tissue expanding membrane to be located in proximal urethral tissues to add bulk to these tissues for overcoming urinary incontinence by localized increase in tissue volume. But the prosthesis does not include any means for post-operative adjustments. U.S. Pat. No. 4,802,479 to Haber et al discloses an instrument for dispensing and delivering material in an inflatable membrane for purposes of a genitourinary prosthesis within the tissues of a patient for overcoming urinary incontinence. However, the inflatable membrane isolated within the tissues is not attached to a conduit and a rear filling means provided immediately below the patient's skin for post operative adjustment or titration of restriction of the urethral lumen. U.S. Pat. No. 4,832,680 to Haber et al discloses an apparatus for hypodermically implanting a genitourinary prosthesis comprising an extensible containment membrane for retaining a fluid or particulate matter which is injected from an external source. But again the distensible membrane is isolated within the patients body tissues and is not connected to a conduit and rear port close to the surface of the skin for post-operative adjustment. Moreover, in an unadjustable device the patient is at risk for retention; where urine cannot be passed because the membrane was initially filled too much causing over restriction of the urethra. Such a condition could lead to kidney damage which would require major corrective surgery or at minimum use of self-catheterization to empty the bladder on a regular basis thus increasing the risk of urinary tract infection (UTI).

U.S. Pat. No. 5,304,123 to Atala et al discloses a detachable membrane catheter incorporated into an endoscopic instrument for implantation into the suburethral region of a patient. Also, U.S. Pat. No. 5,411,475 to Atala et al disclose a directly visualized method for deploying a detachable membrane at a target site in vivo.

In all of these prior art devices, the expandable membrane is delivered to the desired location through an outer tube means. The absences of this requirement in the present invention allows the device to be smaller in diameter, thus allowing it to be delivered through a smaller less traumatic surgical tract.

Also, the present invention utilizes an expandable element attached remotely to a conduit to facilitate delivery or removal of fluid from the expandable element via a rear port which is in close proximity to the patient's skin.

In the present invention, the presence of the port located near the surface of the patient's skin affords the additional advantage of allowing the device to be easily removed through a small incision in the skin if, for instance, it was to become infected or malfunction, whereas all the prior art devices would require major surgery. Furthermore, the presence of the conduit and rear port left in the device delivery tract will serve to prevent backward migration of the expandable element along the tract, a problem which has been noted with prior art devices.

Ideally, if a patient's situation at some future time requires a desirable addition or removal of material to or from the expandable membrane to adjust the restriction and provide a resultant greater/lesser pressure and resistance on the urethra, it is desirable if material could be conveniently adjusted in the membrane. Therefore, the intent of the present invention is to allow a more normal voiding process while maintaining continence in the patient. This post-operative adjustment feature promotes normal voiding patterns for the patient, and appropriate vesicourethral pressure during voiding.

Post-operative adjustment could be done in a semi vertical or horizontal position with the bladder full after anesthesia is resolved and edema is minimal. Adjustment of the expandable element could be done by palpating the rear port which contains a septum for either filling or removing fluid to further titrate the volume of the expandable membrane. This will allow more natural voiding while maintaining continence for the patient.

Because the prior art has not disclosed the components of the present invention, if a physician were to undertake subsequent membrane size adjustments with the prior art devices the following steps would need to be accomplished to make the expandable membrane adjustable post-operatively:

(a) in vivo visualization of the membrane and delivery of a needle deep into the tissue site where the membrane implant resides;

(b) access the inside of the membrane by puncturing it to add or remove material from the membrane, so as to increase or decrease patient urethral restriction; and (c) sealing the membrane so that subsequent loss of fluid does not occur.

Thus, an important medical need exists for an improved implantable device having an expandable membrane element that incorporates a permanently attached conduit and rear port which can be accurately delivered adjacent to a desired body lumen site in a patient, and to which suitable fluid material can be conveniently and reliably added or removed as required.

The primary purpose of the invention is to provide an adjustable implantable device which will restrict urine from involuntarily escaping from the bladder, thus establishing continence for the patient. This adjustable component can be done in a post-operative manner once the patient has resume daily activity via an evaluation to determine what activities cause bladder stress and observable incontinence.

SUMMARY OF INVENTION

The present invention provides an implantable device for adjustably restricting a body lumen, and is suitable for treating both males and female persons and primarily those having stress incontinence. Involuntary loss of urine, for example, may occur when a person may sneeze, cough or laugh, in which the intraabdominal cavity pressure increases thus forcing urine out of the bladder and causes the person to become incontinent. This incontinent condition may exist especially with women who have had multiple child births due to the fact that the anatomy has often times been shifted and the urethra no longer has a normal anatomical position nor does the surrounding tissue have the muscle tone necessary to reliably support the bladder in its normal position.

It is an object of the present invention to overcome this incontinence problem by positioning an implantable device adjacent to at least one side of a patient's urethra so as to adjust liquid flow resistance in the urethra. This is accomplished by having the inner surfaces of the urethra contact each other and thereby provide sufficient flow resistance, so that when pressure is exerted on the bladder the urethra does not open and discharge urine. Moreover, whenever the bladder moves anatomically down because of lack of muscle tone of the pelvic floor, the urethra remains coapted, (i.e. stays closed) and urine does not flow out of the bladder and urethra and the patient is continent.

An important improvement provided by the present invention resides in the ability to access the implanted port element located close to the surface of the patient's skin and adjustably restrict the urethra. This is accomplished by controlling the volume of flowable material in the expandable element after it has been implanted in the patient. The post implantation urethral restriction is realized by the membrane element acting on tissue adjacent to the walls of the urethral lumen and forcefully closing the urethral lumen. Voiding of urine from the bladder only occurs when the intravesicular pressure over comes the resistance established by the expandable element.

Accordingly, this invention provides an implantable device which includes a forward expandable element which can have generally ellipsoidal or spherical shape attached pressure-tightly to an intermediate elongated flexible conduit element, which is flow connected to a rear port portion filling element. An important feature of the implantable device of the present invention relates to an expandable element or membrane which is accessible for subsequent adjustment in volume through the rear port portion located remote from the expandable membrane element and near but under a patient's skin. Another important feature of the present invention over the prior art device is the convenient adjustability of the forward expandable element for pressure and size while in vivo.

Although this invention is useful for both male and female persons, it is generally described as it relates to females and its effect immediately adjacent the urethra wall tissues. Use of the implantable device in females may take place by its being inserted through a small surgical incision made at one or two opposite sides of and in the same body plane as the meatis opening of the female urethra. Delivery of the device is effected by an elongated guide probe member inserted along either side of the urethra. After the delivery guide member is in position in the patient's body, the implantable device with its forward expandable membrane element in a deflated condition is delivered along the guide probe to near the bladder neck. The intermediate conduit element must be sufficiently flexible to permit delivery of the device along the guide probe member inserted into a outer passageway in the device.

Twists or coils in the implanted device connecting conduit tubing may permit the body tissue to grow around it and further anchor the device in the patient's body. The device connecting tubing has sufficient longitudinal stiffness in order to allow insertion over the guide probe and to minimize collapse and migration, and is made of a bio-compatible material such as silicone rubber. The septum element is usually a single element for each expandable element implanted, however, a single septum element could be used for providing fluid to more than one expandable element. The septum element is usually disc shaped and made of silicone rubber.

The device according to the invention is intended to work immediately adjacent to the urethral wall of a patient to create an increase in urethral coaptation and flow resistance. However, in the prior art devices any tissue change which may occur post-operatively such as a reduction in tissue edema associated with the procedure may cause a reduction in clinical effect because of the reduced coaptation and resistance after the swelling has subsided. Although some minor degree of adjustability is available at the time of implantation in the prior art devices, not until availability of the present invention is it possible to access the implanted device and adjust the membrane volume after implantation in a post-operative manner.

The present invention also provides an implantable device delivery assembly which is a significant improvement over the prior art, especially with regard to the mechanism and method of in vivo adjustability of the implanted membrane element as a convenience to both the patient and the physician. The equipment assembly for delivery and activation includes three essential members, which are—a location guide probe member for delivery of the implantable device and its placement in the body of a patient, and a source of suitable flowable material such as a syringe for injection of the desired flowable material into the implantable device rear port element.

In order for the implanted device to act on the urethra of a patient, it must be properly located in the patient's body tissue to permit the membrane element to act correctly upon the urethra and effect its coaptation. After the desired insertion site for the implantable device is located and it is delivered to that site, the implanted membrane element which is flow connected to the remote rear port through the connecting conduit is accessed via the rear port to deliver a flowable material causing expansion of the membrane. Because the rear port portion is placed just under the patient's skin, thereafter adjustment of the membrane pressure and size is relatively simple, by accessing the rear port septum for the addition or removal of flowable material into or from the membrane.

While this invention has utility by effecting urethral coaptation for both male and female patients, the mode of delivery of the device to the site makes it somewhat easier to use for females due to anatomical differences. The invention as described herein relates to its use for female patients. According to its method for use, a physician will initially make a small incision at either side of the meatis, i.e. opening of the female urethra. This incision(s) permits a delivery guide probe member to be inserted into the body tissue alongside of the urethra so as to define the path of later entry for the implantable device. Next, delivery of the device along the guide probe is made on either one or two opposite sides of the urethra, one placement at a time. Lastly, the implanted device with the expandable membrane element directed to each location is left in place, with access for adjustment of the membrane size being available through a remote elastic septum in the rear port away from the expandable membrane and located immediately under the skin of the patient.

In actual use, two of the devices are usually implanted on opposite sides of the urethra so as to effect a balanced urethral coaptation and resistance. If after implantation inflation of the expandable membrane is excessive, thereby creating a disproportionate urethral resistance by obstructing the patient and causing a bladder pressure higher than normal during voiding, damage to the bladder and kidney may ensue. Thus, a post-operative membrane size adjustment is available to reduce the patient's bladder pressure during voiding and maintain intravesicular pressure within normal limits.

In actual use, it is preferred to implant two individual devices with individual septums located on opposite sides of the urethra. Alternatively, the device may be so configured to have one septum serve both expandable membrane elements. The volume for the respective expandable membranes can be adjusted up or down by introducing or removing fluid through a syringe needle inserted into the septum. Suitable flowable materials for introduction into the expandable membrane include a saline liquid, a flowable gel, or a slurry of small particles such as silicone in a fluid carrier. Moreover, the flowable material may be made radiopague to facilitate fluoroscopic visualization for post-operative inspection. After implantation and a period of time has transpired allowing induced edema during the procedure to subside, the patient should be evaluated. At that time of evaluation, if the patient is not voiding in a normal manner, post-operative adjustments can be made via the rear port access. During the membrane adjustment procedure, the syringe needle is directed into the device septum to adjust the membrane with a flowable material. The needle is provided with a sharp non-coring end to allow the introduction of material into the membrane. A needle stop within the septum may also be provided to facilitate correct positioning of the needle and also reduce risk of piercing the needle completely through the septum. All of the components are either bonded or molded to one another prior to its implantation.

With the present invention, the membrane configuration is optimized for its intended purpose and the design of the septum is also optimized for post-operative adjustment of the membrane size. In the prior art, if post-operative adjustment was attempted the physician would have had to identify and locate the membrane deep within the tissue, puncture the membrane with an elongated needle and either remove or add fluid to decrease or increase urethral resistance effects respectively. But for the present invention, it is not necessary to puncture the membrane for size adjustment and therefore membrane integrity is maintained. Furthermore, for the present invention it is not necessary to visualize the expandable element to make in vivo adjustments because of the remote port located in close proximity to the patients skin in which adjustment can be made easily. All of the aforementioned features of the present invention contribute towards maintaining integrity of the expandable membrane and affording easy access to and adjustment of the expandable element in a post-operative manner.

BRIEF DESCRIPTION OF DRAWINGS

This invention will now be described further with reference to the following drawings:

FIG. 2 is a longitudinal cross-sectional view of the implantable device shown in FIG. 1;

FIG. 3 is a cross-sectional view taken along line 3—3 of FIG. 2;

FIG. 4 illustrates a guide probe member inserted into body tissue to an implant location adjacent a body lumen of a patient prior to insertion of the implantable device;

FIG. 5 shows the implantable device placed over the guide probe member and partially advanced to the desired location with the expandable element being deflated;

DESCRIPTION OF INVENTION

Figure 1:
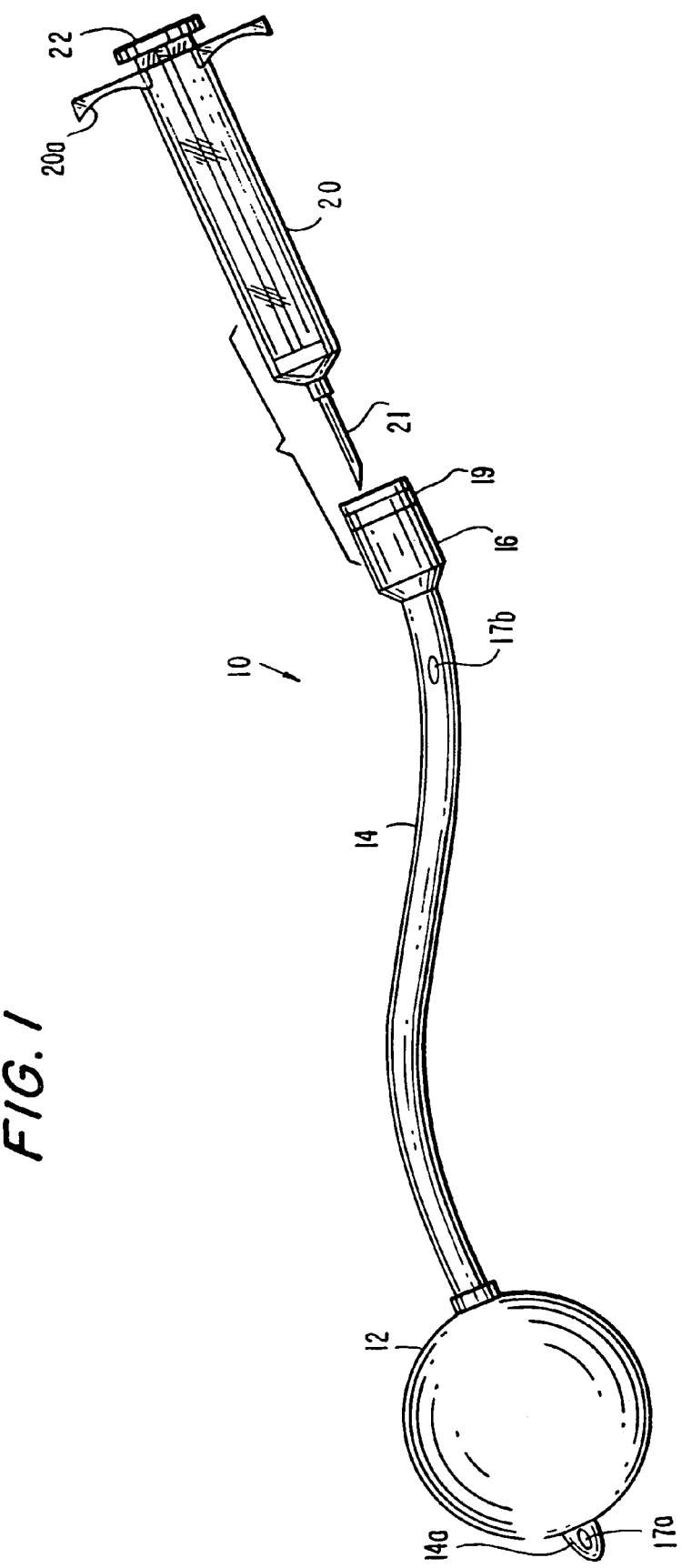
FIG. 1 is a perspective view of the implantable device and its assembly with a syringe source for providing a flowable material to a forward expandable element according to the present invention.

According to the present invention as shown by FIG. 1, there is provided an elongated implantable device 10, which includes a forward expandable membrane element 12 shown in its full expanded size, and is attached pressure-tightly to a central conduit element 14 having a rearward port portion 16 which communicates with the expandable element 12 through an inner passageway 15 (see FIG. 2). The conduit 14 has a pointed forward end 14a which extends slightly beyond the expandable element 12. A syringe 20 including a hollow needle 21 and a rear axially-movable plunger 22 is provided for adjustably injecting a suitable flowable material into the device 10 through the rear port portion 16 to expand the membrane element 12.

As further shown in FIGS. 2 and 3, the central connecting conduit 14 contains two elongated lumens or passageways. The first lumen 15 provides an internal passage by which the flowable material is directed from a cavity 16a in the rear port 16 to expand the expandable element 12 such as a membrane or balloon. The conduit 14 is attached integrally to the port element 16 at its rearward end. The second lumen 17 extends from a front opening 17a to a rearward opening 17b and serves to receive an elongated guide probe (see FIG. 4) and effect delivery of the implantable device 10 to a desired location in the body tissue of a patient.

An important feature of the implantable device 10 having the first lumen 15 includes a first opening port 15a located in cavity 16a of the port portion 16 between an elastic septum 18 and the conduit 14 and is connected to the device first lumen 15, so that a flowable material can be infused therethrough, and a second port 15b serves to direct the working fluid to the expandable membrane element 12.

During adjustment of the volume of the membrane fluid provided from a hollow needle 21 of syringe 20, is infused through the septum 18 and continues on through the conduit tubing 14 connected to the expandable membrane element 12. The port portion 16 preferably has a diameter greater than conduit 14 so as to accommodate the cavity 16*a* and elastic septum 18, which is retained securely by a clamp ring 19.

The entire implantable device 10 including the expandable membrane element 12 is formed of a biocompatible material such as silicone or polyurethane elastomer, and the device conduit 14 and port 16 may be formed as a unitary construction. Optionally, the membrane element 12, the rear port 16, and connecting conduit tube 14 can be molded as one piece. As shown in FIG. 2, the expandable membrane 12 is adhered at 13 to conduit tube 14 at its forward end by a suitable adhesive material.

The implantable device and assembly according to this invention includes three main members. The first member provided is an elongated guide in the form of a stiff solid elongated guide probe 24 (see FIG. 4) adapted for delivery of the implantable device 10 to the desired site in the body tissue of a patient as generally shown by FIGS. 4 and 5. Alternatively, the elongated guide member can be in the form of a flexible guidewire which has been initially delivered into the body tissue through a separate hollow stiff probe that has been inserted to the desired location in the body tissue. The second member of the assembly is the implantable device 10 which includes the expandable membrane element 12 and conduit 14 containing the two lumens or passageways 15 and 17 and having the rear port portion 16. In use, the implantable device 10 is guided to a pre-determined location adjacent a body lumen in a patient's body after the elongated solid guide probe 24 is first surgically inserted into the body tissue of the patient to establish an initial pathway. The lumen forward end opening 17*a* of device 10 is then disposed over the rear end of probe 24 to guide the device 10 and deliver the expandable membrane 12 (in its contracted shape 12*a*) to the pre-determined location in the body tissue adjacent to the lumen which is to be adjustably restricted. The diameter of passageway 17 is made slightly larger than that of the probe member 24 to permit the device 10 to slide easily over the probe member.

During actual use, a physician will first make a small incision in the skin 30 of the patient near the restrictable body lumen 32, and then by visualization means such as fluoroscopy the solid guide probe 24 is directed to the desired location, depending upon the anatomy of the patient. Thereafter, the device second lumen forward opening 17*a* of the conduit 14 with the expandable membrane 12 in its initial deflated or contracted condition or shape 12*a*, is slid over the rear end 24*a* of the delivery guide 24. The delivery guide slides through the second lumen 17 of conduit 14 and exits at rearward opening 17*b*. As illustrated in FIG. 2, opening 17*b* occurs between expandable element 12 and rear port portion 16. However it might be advantageous to locate opening 17*b* close to expandable element 12 or, alternatively, to have the lumen 17 extend through the rear port portion 16.

If desired, a detent or mark 33 may be provided on the solid probe 24 which when aligned with a feature on the device 10 such as rear port 16 will assure that the device 10 is appropriately placed at the correct depth in the patient's body tissue 30. It may be necessary to provide the device central conduit 14 in multiple lengths to facilitate placement of the septum 18 near the patient's skin. Alternatively, the conduit 14 effective length could be made adjustable by it having a helical shape similar to that of a coiled spring.

After implantable device 10 has been advanced over guide probe 24 so that the contracted member 12*a* is in the desired position adjacent to the body lumen 32, the body lumen 32 may be restricted to a desired degree by piercing septum 18 with the needle 21 of syringe 20 and injecting a flowable material through passageway 15 into the expandable element 12. The physician may determine the desired degree of restriction of body lumen 32 by means such as infusing fluid through the body lumen past the restriction and measuring the back pressure.

Figure 6:
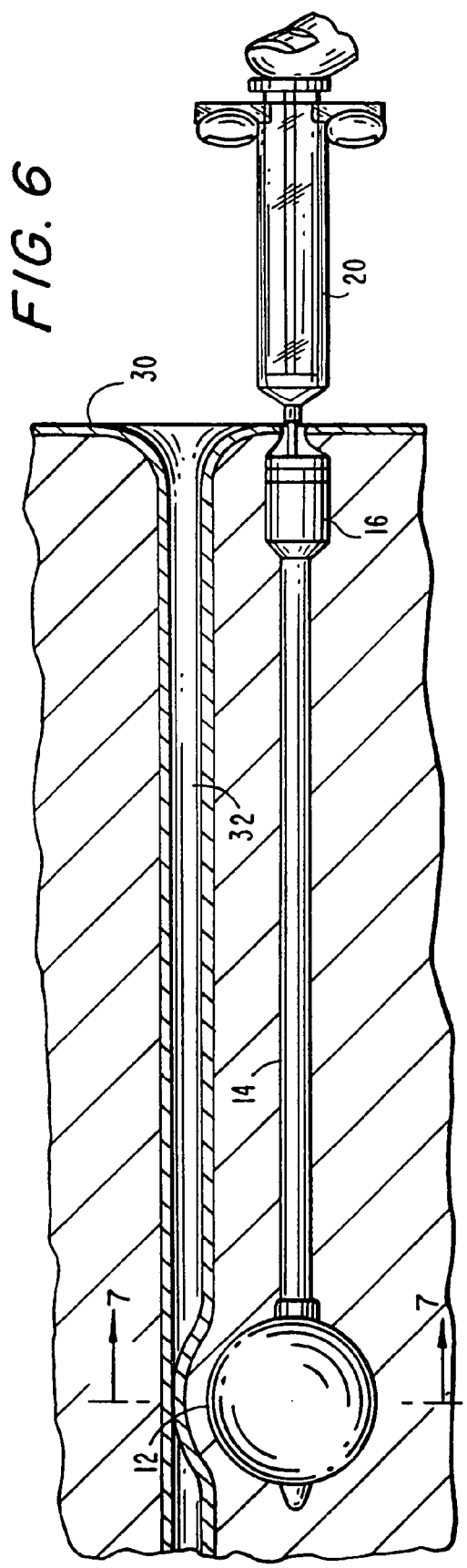
FIG. 6 shows the implanted device assembly after being expanded at the desired location in the body tissue of the patient so as to displace body tissue toward the body lumen for causing adjustable restriction of the body lumen.

As illustrated by FIGS. 1 and 6, the source of flowable material is usually a syringe 20 with a hollow needle used to pierce the elastic septum 18, however alternate fluid containers with means for making a reversible connection to device 10 could be used. The flowable material may be, for example, a saline solution, a flowable gel, or a slurry of particles in a liquid carrier. It may be advantageous to make the flowable material radiopaque so that the degree of membrane inflation may be viewed by x-ray.

An alternative method of delivery of the device 10 could be to first withdraw solid probe 24 from the body tissue and then inflate expandable member 12. A further alternative would be to first place device 10 over the solid guide probe 24 outside the body and then insert them both into the body tissue as a unit. To facilitate this latter procedure, it may be desirable that there be some friction between solid guide probe 24 and the second lumen 17 in conduit 14.

Figure 8:
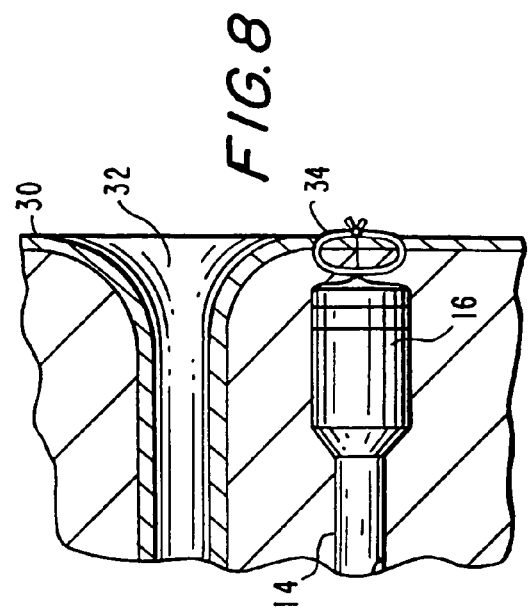
FIG. 8 shows the implantable device rear port portion after being inserted near but below the skin of a patient.
Figure 7:
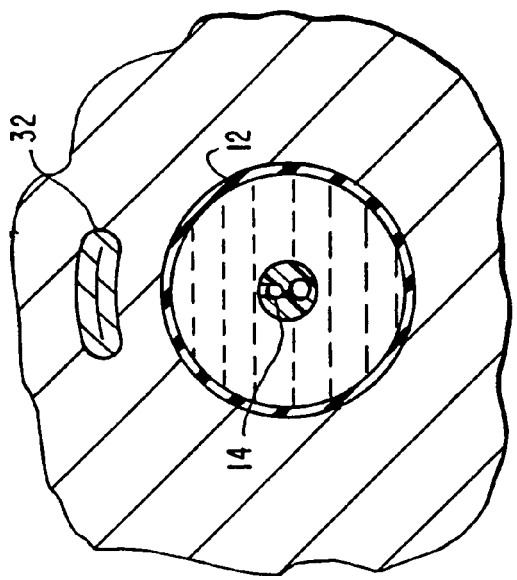
FIG. 7 is a cross-sectional view taken along line 7—7 of FIG. 6.

After the implantable device has been properly positioned with the expandable member 12 located near the body lumen 32 and the septum in rear port 16 located near the skin 30, the device is injected with a flowable material from the syringe 20. Once filling of the expandable member is complete, the solid probe 24 is withdrawn from the device leaving the expanded membrane element in the body tissue. Then the skin incision 31 is closed over the port 16 by means such as a suture 34 as shown in FIG. 8.

As described, an essential feature of this invention relates to adjustability of the membrane expansion post-operatively. This adjustability is effected because the septum 18 is located remote from the expandable membrane element 12 but near and under the patient's skin. The port and septum is located by, for instance, manual palpation of the skin region and the needle of the syringe is inserted through the skin and septum so as to add or remove material from the expandable member, thus increasing or decreasing the restriction of the body lumen.

To assure proper sealing of the septum element 18, it is placed in compression within cavity 16*a* by providing a tight metal ring 19 which surrounds the port 16 and is smaller in diameter than the port. When the needle 21 of syringe. 20 is withdrawn from the septum 18 after expansion or adjustment of the expandable element 12, there is positive sealing around the perimeter of septum 18.

FIGS. 4–8 generally illustrate the method or procedure for properly implanting the device 10 in the body tissue of a patient. As shown by FIG. 4, a physician after locating the body lumen such as a female urethra of a patient, first make a small incision 31 and inserts the guide probe 24 in the body tissue to a desired location adjacent the body lumen 32. This procedure is usually carried out under a local anesthetic with visual guidance, for instance under fluoroscopy by the physician. Next, the physician takes implantable device 10 and places it over the probe member 24, through the second lumen 17 per FIGS. 1 and 2, the probe 24 entering at forward opening 17*a* and exiting at the rear opening 17*b*. The device 10, for which connecting conduit 14 is sufficiently flexible, is advanced along the probe 24 into the body tissue 31.

After the desired location within the body tissue 30a has been reached, a suitable flowable material is introduced into the device 10 from a source such as the syringe 20 having hollow needle 21 inserted through septum 18 so as to at least partially expand the membrane 12, as shown by FIG. 6. Next the probe 24 is removed and the membrane 12 is expanded further to the desired enlarged size for restriction of the body lumen 30. The syringe 20 is removed from the device 10, after which the desired size of expanded membrane 12 is maintained by the elastic septum 18. Next, the patient's incision at 31 is surgically closed over the port 16 and septum 18 by sutures at 34.

Although this invention has been described broadly and in terms of preferred embodiments, it will be understood that modifications and variations can be made within the scopes as defined by the following claims.

We claim:

1. An implantable device, comprising:
  a pressurizable expandable element, attached to an elongate conduit element near its forward end, said conduit element including a rear port portion and having a first passageway connecting said rear port portion to said expandable element, said expandable element expandable to enlarged shapes by addition of a flowable material using an external source provided into said rear port portion, said rear port portion adapted for providing fluid communication between the implantable device and the external source during adjustment and for automatically sealing the flowable material in the implantable device upon removal of the external source,
  wherein the implantable device is adapted for implantation within body tissue with the expandable element adjacent a body lumen to provide volume to the body tissue for adjustable coaptation of the body lumen.

2. The implantable device according to claim 1, wherein said rear port portion comprises an elastic septum.

3. The implantable device according to claim 1, wherein said elongate conduit has a second elongate passageway extending from an opening in the conduit forward tip end to a location rearward from said expandable element.

4. The implantable device according to claim 1, wherein said expandable element is attached onto said elongate conduit element by a material comprising an adhesive material.

5. The implantable device according to claim 1, wherein said elongated conduit element permits subcutaneous positioning of the rear port portion.

6. The implantable device according to claim 1, wherein the implantable device is constructed using a bio compatible material such as polyurethane or silicone.

7. The implantable device according to claim 1, wherein the rear port portion comprises a compression ring for maintaining a seal of the rear port portion.

8. An implantable device assembly, comprising:
  (a) an elongate guide probe member adapted for being inserted into tissue adjacent a body lumen of a patient;
  (b) an elongate implantable device adapted for being surgically implanted into the tissue adjacent to the body lumen, said implantable device including a forward expandable element and a rear port portion connected together by flexible conduit, said conduit having a first inner passageway in fluid communication between said expandable element and said rear port portion and having a second passageway adapted for receiving said elongate probe member; and
  (c) an external source containing a flowable material and adapted for connection to the rear port portion of said implantable device, whereby a flowable material from said external source can be introduced through the rear port portion and through the first passageway of said implantable device so as to expand the forward expandable element adjacent a body lumen to at least partially and adjustably restrict the lumen.

9. The implantable device assembly of claim 8, wherein said guide probe member comprises a stiff elongate rod having a pointed forward end.

10. The implantable device assembly of claim 8, wherein said guide probe member comprises a flexible guidewire.

11. The implantable device assembly of claim 8, wherein said implantable device rear port portion contains an elastic septum and said source is a syringe having a forward facing needle whereby said needle may be sealingly inserted in said septum and a flowable material injected from said syringe through the first passageway to expand the forward expandable element.

12. The implantable device assembly of claim 11, wherein said syringe includes an axially movable rear plunger element, whereby the needle is insertable into the elastic septum located in the rear port portion of the implantable device and a flowable material injected by the plunger element through the needle and first passageway to expand the forward expandable element.

13. A method for variably restricting a body lumen in a patient, comprising the steps of:
  guiding an elongate implantable device into body tissue of a patient to a location adjacent a body lumen to be restricted using an elongate probe member, the elongate implantable device having an expandable element located at its forward end and having a port portion provided at its rearward end, so that the expandable element is positioned adjacent to the body lumen; and
  providing a flowable material from a source into the port portion in fluid communication with the expandable element, and at a location separate from the expandable element, so as to expand the expandable element to at least partially restrict the body lumen, wherein the implantable device is guided over the elongate probe member.

14. The method of claim 13, further comprising the steps of:
  withdrawing the elongate probe member from the patient's body;
  positioning the port portion of said elongate implantable device inside the patient's body tissue near the surface of the skin, and
  closing an opening made in the patient's skin over the port portion.

15. The method of claim 13, wherein the step of providing a flowable material includes injecting one or more of a saline liquid solution, a gel, or a slurry of particles in a fluid carrier.

16. The method of claim 13, wherein the step of providing a flowable material includes injecting a radiopaque material to facilitate fluoroscopic visualization.

17. The method of claim 13, wherein the elongate probe member and implantable device are surgically inserted to a location adjacent the urethra of a patient.

18. The method of claim 13 including placing an implantable device along two opposite sides of the urethra of a patient.

19. The method of claim 13, wherein the implantable device is guided over the elongate probe member.

20. The method of claim 13, wherein the implantable device and elongate probe member are inserted into the body tissue as a unit.

21. The method of claim 13, wherein the implantable device is positioned using visual guidance.

22. The method of claim 13, wherein the implantable device is positioned using fluoroscopy.

23. The method of claim 13, further comprising:
increasing restriction of the body lumen by adding flowable material to the implantable device.

24. The method of claim 13, further comprising:
decreasing restriction of the body lumen by removing flowable material from the implantable device.

25. The method of claim 13, further comprising:
measuring restriction of the body lumen by infusing fluid through the body lumen past a restricted portion of the body lumen and measuring back pressure.

26. The method of claim 13, wherein providing a flowable material from a source into the port portion comprises:
injecting the flowable material into a septum of the port portion using a hyperdermic needle.

27. The method of claim 13, further comprising:
expanding the expandable element prior to withdrawal of the elongated probe member.

28. A method for variably restricting a body lumen in a patient, comprising:
guiding an elongate implantable device into body tissue of a patient to a location adjacent a body lumen to be restricted using an elongate probe member, the elongate implantable device having an expandable element located at its forward end and having a port portion provided at its rearward end, so that the expandable element is positioned adjacent to the body lumen; and
providing a flowable material at the rearward end from a source directly to the port portion, so as to expand the expandable element to at least partially restrict the body lumen;
wherein the implantable device is positioned using fluoroscopy.

29. The method of claim 28, further comprising:
withdrawing the elongate probe member from the patient's body;
positioning the port portion of said elongate implantable device inside the patient's body tissue near the surface of the skin, and
closing an opening made in the patient's skin over the port portion.

30. The method of claim 28, wherein the material includes injecting one or more of a saline liquid solution, a gel, or a slurry of particles in a fluid carrier.

31. The method of claim 28, wherein providing a flowable material includes injecting a radiopaque material to facilitate fluoroscopic visualization.

32. The method of claim 28, wherein the elongate probe member and implantable device are surgically inserted to a location adjacent the urethra of a patient.

33. The method of claim 28, including placing an implantable device along two opposite sides of the urethra of a patient.

34. The method of claim 28, wherein the implantable device is guided over the elongate probe member.

35. The method of claim 28, wherein the implantable device and elongate probe member are inserted into the body tissue as a unit.

36. The method of claim 28, further comprising:
increasing restriction of the body lumen by adding flowable material to the implantable device.

37. The method of claim 28, further comprising:
decreasing restriction of the body lumen by removing flowable material from the implantable device.

38. The method of claim 28, further comprising:
measuring restriction of the body lumen by infusing fluid through the body lumen past a restricted portion of the body lumen and measuring back pressure.

39. The method of claim 28, wherein the step of providing a flowable material from a source into the port portion comprises:
injecting the flowable material into a septum of the port portion using a hyperdermic needle.

40. The method of claim 28, further comprising:
expanding the expandable element prior to withdrawal of the elongated probe member.

* * * * *